United States Patent [19]

Diepers

[11] 4,412,316
[45] Oct. 25, 1983

[54] ULTRASONIC TRANSDUCER ARRANGEMENT

[75] Inventor: Heinrich Diepers, Höchstadt, Fed. Rep. of Germany

[73] Assignee: Siemens Aktiengesellschaft, Berlin and Munich, Fed. Rep. of Germany

[21] Appl. No.: 265,448

[22] Filed: May 20, 1981

[30] Foreign Application Priority Data

May 21, 1980 [DE] Fed. Rep. of Germany ....... 3019409

[51] Int. Cl.³ .......................... G01S 15/02; G01S 7/54
[52] U.S. Cl. ..................................... 367/105; 73/626; 367/122; 367/123
[58] Field of Search ....................... 367/105, 122, 123; 73/626

[56] References Cited

U.S. PATENT DOCUMENTS 3,936,791 2/1976 Kossoff ............................ 367/103 X
4,131,023 12/1978 Mezrich et al. .................. 73/626 X
4,219,846 8/1980 Auphan ............................ 73/626 X
4,307,613 12/1981 Fox .................................. 367/105 X

OTHER PUBLICATIONS

"Ultrasonic Imaging", vol. 1, No. 1, 1979; pp. 56-75; D. R. Dietz, S. I. Parks, and M. Linzer.

*Primary Examiner*—Richard A. Farley
*Attorney, Agent, or Firm*—Kenyon & Kenyon

[57] ABSTRACT

An ultrasonic transducer arrangement having ultrasonic oscillators, with which electronic delay chains are associated, includes a matrix of column-like ultrasonic oscillators the end faces of which are each connected to control electrodes arranged in the planes of the flat sides of the matrix. On one flat side of the matrix, rows of the oscillators are each provided with a common control line and, on the opposite flat side of the matrix, the jointly controlled groups of ultrasonic oscillators each form a concentric arrangement. This test head can be used selectably as a focusing or as an angle test head and in addition, the focal point can also be displaced in depth.

9 Claims, 2 Drawing Figures

ULTRASONIC TRANSDUCER ARRANGEMENT

BACKGROUND OF THE INVENTION

This invention relates to ultrasonic transducers in general and more particularly to an ultrasonic transducer arrangement which includes ultrasonic oscillators having associated electronic delay chains.

A multiplicity of transducer elements which can be excited differently as to phase and amplitude by means of electronic control members are used in a known transducer arrangement. By changing the amplitude and phase drive of these so-called phased arrays, the radiated and received sound field can be influenced so that angle testing heads and focusing heads can be replaced by a single array test head. The linear propagation time delay of the ultrasound pulses provides tilting, and, through symmetrical, for instance, square law delay of the ultrasound pulses, focusing of the sound field is obtained. By superimposing a linear and a square law delay, the sound field is focused as well as tilted in the longitudinal direction of the transducer arrangement. With an adapter section acting as an acoustical lens, the sound field can additionally be focused in the plane transverse to the longitudinal direction of the transducer arrangement. Focusing is limited to a value, however, which is given by the curvature of the lens (U.S. Pat. No. 3,936,791).

Ultrasonic transducer arrangements with transducer elements in the form of a matrix for producing sectional images of a body to be examined with ultrasound, so-called B-displays are already known (German Pat. No. 28 29 570).

Also known are ring arrays, in which ring shaped ultrasonic oscillators are controlled independently of each other and the aperture angle is changed by adding or disconnecting outer rings and the so-called natural focal point is thereby displaced when transmitting. A so-called breathing aperture is obtained. For receiving, a dynamic focal point, the depth of which can be changed continuously, is generated by continuous electronic phase control. This dynamic focusing, however, requires a relatively large amount of electronics ("Ultrasonic Imaging," vol. 1, no. 1, 1979, pages 56 to 75).

SUMMARY OF THE INVENTION

It is now an object of the present invention to describe an ultrasonic transducer array which can be used selectably as a normal test head, an angle or also focus test head as well as a focusing angle testing head and which is suitable for displacing the focal point in the depth of the body to be examined.

The present invention is based on the discovery that with special contacting and drive of the ultrasonic oscillators within a matrix, in conjunction with the well-known phase delayed drive, the functions of the different test heads can be combined in a single electronic test head. Thus, the present invention includes:

a. a matrix of ultrasonic oscillators, the end faces of which are arranged in the plane of one of the flat sides of the matrix, each oscillator connected to a control electrode;

b. on a flat side of the matrix, a common control line for each row of ultrasonic oscillators; and c. on the opposite flat side of the matrix, a common control line connected to electrodes of ultrasonic oscillators arranged concentrically to each other.

The combination of the different functions is obtained by the special contacting of the ultrasonic oscillators on the two flat sides of the matrix in conjunction with the possibility of driving the electrodes on one of the flat sides either with delay or applying to them a common potential, preferably zero potential.

If zero potential is applied to the ultrasonic oscillators connected in groups to concentric electrodes on one flat side of the matrix, and the ultrasonic oscillators on the other flat side of the matrix are driven in rows jointly without delay, the radiation into the workpiece to be tested takes place perpendicularly to the flat sides of the matrix. If the rows of ultrasonic oscillators are each preceded by a transmitter of a transmitter chain as well as by a delay stage of a linear electronic delay chain, and if such a linear delay chain is also associated with the receiver, the workpiece can be insonified successively with different angles. The magnitude of the angle is determined by the delay. With, for instance, square law delay, transmitting and receiving takes place perpendicularly to the matrix with a focus which can be set by the delay. The focal point can therefore be placed at different depths of the workpiece to be examined. Through the superposition of a linear and square law delay, the insonification is accomplished with adjustable angular direction and adjustable focus. The radiation angle can be selected by adjusting the linear delay, and the depth of focus by adjusting the square law delay.

If the rows of the oscillator electrodes on the other flat side of the matrix of the transducer array are connected to zero potential and the concentric electrode connections on the one flat side of the matrix are driven with square law delay, focusing in the plane perpendicular to the rows of electrodes of the ultrasonic oscillator with perpendicular direction of radiation, as well as also in the plane in their longitudinal direction is obtained. A "focal tube" is thus obtained by this three-dimensional focusing.

In a particularly advantageous embodiment of the transducer array, the individual ultrasonic oscillators are subdivided in still at least another direction transversely to their longitudinal axis into a group of acoustically separate transducer elements which are driven together electrically. In a special embodiment, a still further subdivision of the transducer elements so produced in their longitudinal direction can be made, so that each ultrasonic oscillator consists of a matrix of jointly driven, column-like transducer elements, the end faces of which are each located on a flat side of the matrix of the overall arrangement. The dimensions of the column-like transducer elements are then preferably chosen so that their length is approximately equal to one-half the wavelength and therefore, about twice as large as their width.

DETAILED DESCRIPTION

Figures 1, 2:
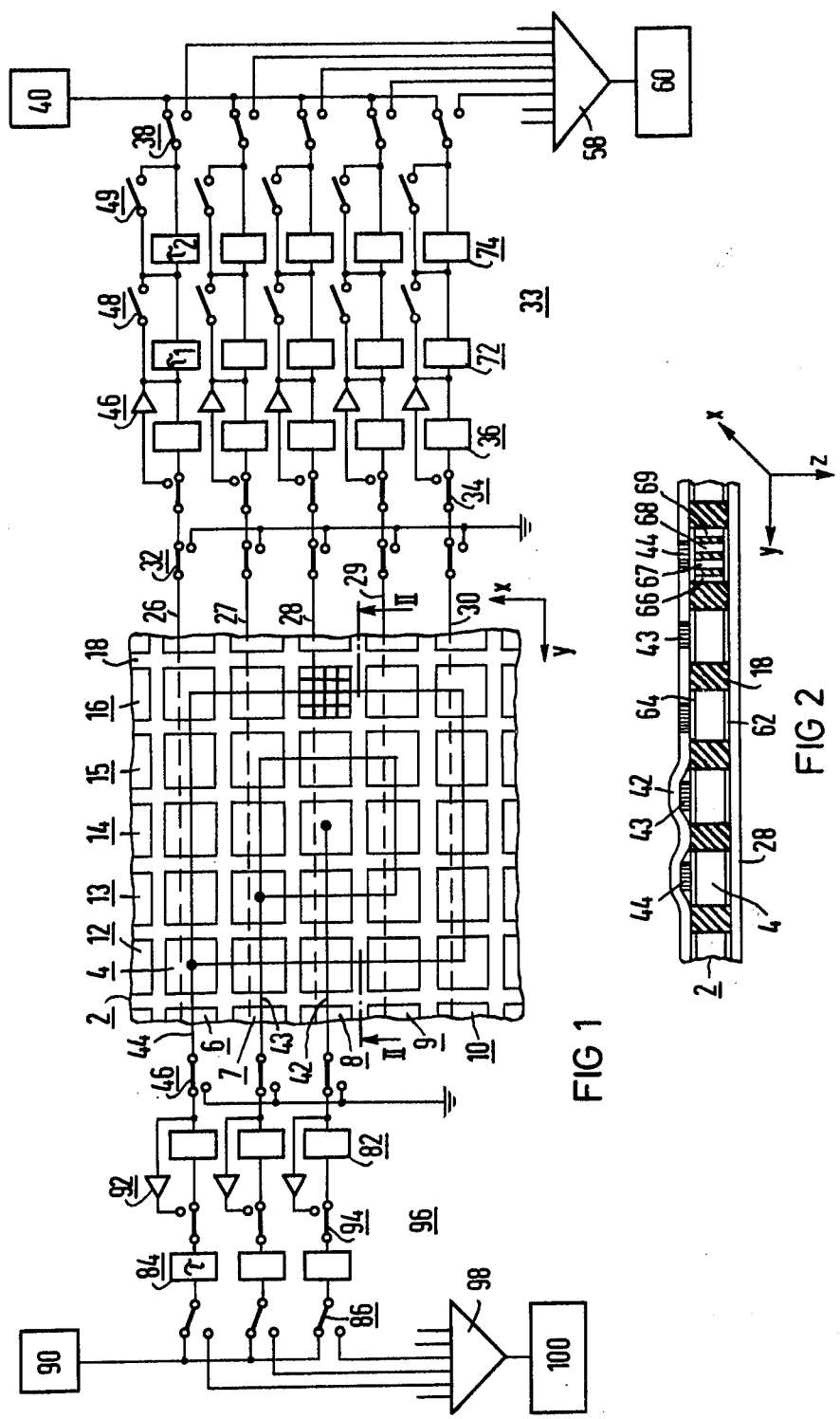
FIG. 1 is a schematic-block diagram of an ultrasonic transducer array according to the present invention, with its electronic control.
FIG. 2 illustrates part of FIG. 1 as a cross-section.

According to FIG. 1, a matrix 2 of ultrasonic oscillators 4 is arranged in rows 6 to 10, one after the other, and in columns 12 to 16, side by side. The spaces 18 between the ultrasonic oscillators 4 are shown enlarged in the figure for better clarity. The column-like ultrasonic oscillators 4 are arranged within the matrix 2 in such a manner that their lower end face lies in the lower flat side of the matrix 2. At the lower flat side of the matrix 2, the ultrasonic oscillators 4 of rows 6 to 10 are each connected via a control line, common to each row, to a transmitter and a receiver. The control conductors 26 to 30 in the figure are used for this purpose. They can be connected to zero potential via a double-throw switch chain 32 which will preferably consist of electronic switches.

However, in the position illustrated, the switches of switch chain 32 connect, via electronic circuitry 33, to the clock generator 40 of the transmitter. Alternatively, by means of switching device 38, the conductors 26 to 30 may be connected to a summing amplifier 58 of a receiver 60 which may, for instance, be an electronic picture screen. The electronic circuitry 33 contains, for each of the rows 6 to 10 of the ultrasonic oscillators, one switch from a chain of switches of an electronic switching device 34. As will be seen below this switching device 34, along with switching device 38 is used to switch between the transmitting and receiving modes. Electronic circuitry 33 also includes transmitters of a transmitter chain 36 and delay member chains 72 and 74, along with associated switches in switch chains 48 and 49 for shorting out the respective delay members. The electronic switching device 34 and optionally also the switching device 38 may preferably be designed as integrated circuits, the blocking attenuation of which may preferably be at least about 40 dB.

At the upper flat side of the matrix 2, a central ultrasonic oscillator, not specifically designated, is connected to a control conductor 42. Groups of the ultrasonic oscillators 4 which surround the central ultrasonic oscillator concentrically are each connected to a common control conductor, the common conductors 43 and 44 being shown in the figure. If zero potential is applied to the control lines 42 to 44 of the electrodes at the upper flat side of the matrix 2, each via a double throw switch of a double throw switch chain 46, the ultrasonic oscillators 4 of the matrix 2 can be driven by means of the clock generator 40 and the transmitter chain 36 in rows via the control lines 26 to 30. Radiation perpendicular to the flat side of the matrix 2 in a test body, not shown in the figure, is then obtained. After the transmitting pulses have been delivered, the electronic switching devices 34 and 38 are switched and the echo signals are generally fed to the receiver 60 via the preamplifier of a preamplifier chain 46 and two electronic switches in series, which belong respectively to the chains of shorted switches 48 and 49, and via electronic switching device 38 which is switched to the summing amplifier 58.

The ultrasonic oscillators 4 can preferably be subdivided by so-called fine subdivision in the x direction as well as in the y direction into a matrix of column-like transducer elements as is indicated in FIG. 1, for simplification, only for one ultrasonic oscillator in row 8. These transducer elements are then contacted jointly at their end and are connected electrically in parallel.

According to FIG. 2, the ultrasonic oscillators 4 are arranged side by side in the direction of the rows 6 to 10 in such a manner that their end faces, each of which is provided with a metal deposit 62 or 64, respectively, lie on one flat side of the matrix. Of the transducer elements generated by the fine subdivision, the front row of one of the ultrasonic oscillators is shown, and these elements are designated as elements 66 to 69. The spaces 18 between the ultrasonic oscillators 2 and optionally also between the transducer elements 66 to 69 are filled with a material, the acoustic impedance of which differs substantially from the impedance of the oscillator material. On the lower flat side, the transducer elements 4, of row 8, are connected by the control line 28. On the upper flat side of the matrix 2, the control conductors 42 to 44 are seen which are brought along the surface. The electric insulation of the control conductors 42 to 44 from each other is not shown in the figure for the sake of simplicity.

If the radiation from the matrix 2 in the xz plane is to take place at different angles relative to the normal on the plane, the control lines 26 to 30 must carry respective electronic delays. This is accomplished with linear delay chain 72, which, with the switch 49 closed and switch 48 open, feed the clock pulses of the clock generator 40 to the transmitters of the transmitter chain 36 with a respective linear delay and feed the echo pulses via the switches of the electronic switching device 34, as well as the preamplifier of the preamplifier chain 46, to the summing amplifier 58 of the receiver 60 with the same delay. By changing the linear delay of the delay chain 72, different radiation angles can be set and the transducer array thus acts like an angle test head. By means of a further delay chain 74, the delay stages of which are adjusted for a square law delay and with which the shorting switches 49 are associated, the ultrasonic oscillators 4 of the matrix 2 can be addressed with a square law delay and the echo pulses can be fed to the receiver with the same delay. For this purpose, the switches of the shorting switch chain 48 are closed and the switches 49 are opened.

If the shorting switches 48 and 49 are opened, the linear delay chain 72 as well as the square law delay chain 74 is operative. Through the superposition of a linear and a square law delay in the drive of rows 6 to 10 of ultrasonic oscillators 4 of the matrix 2, tilting as well as focusing of the radiated sound field is possible.

In a particularly advantages embodiment, the concentric electrode groups of the upper flat side of the matrix 2 can each be connected via the control line 42 to 44 to a transmitter and a receiver. For this purpose, the control lines each contain a transmitter of a transmitter chain 82 and an electronic delay stage of a delay chain 84 with square law delay, which is connected, via a respective double throw switch of an electronic switching device 86, to either the clock generator 90 of a transmitter or to the summing amplifier 98 of a receiver 100. The transmitted pulses are fed from the clock generator 90 via the transmitter chain 82 to the ultrasonic oscillators 4 of the respective oscillator group with a delay which is set at the delay stages of the delay chain 84. At the lower flat side of the matrix 2, rows 6 to 10 of the ultrasonic oscillators 4 are connected to zero potential via the double-throw switch 32. The echo signals are fed, via respective preamplifiers of a preamplifier chain 92 as well as a further electronic switching device 94 and the same delay stages of the delay chain 84 as well as the accordingly switched electronic switching device 86 and the summing amplifier 98, to the picture screen of the receiver 100. By changing the time delay of the delay chain 84, the amount of focusing and thereby, the depth of the focal point within the object to be tested can be set.

In the illustrated embodiment, the control lines 43 and 44 connect square-law electrode groups which are arranged concentrically to each other. In some cases it may be advantageous to form ring shaped or also star shaped electrode groups by suitable contacting. With such special forms of the excitation geometry and therefore of the aperture of the transducer array, side lobes in the radiation characteristic of the transducer array, for instance, can be suppressed.

Through the particular type of drive for rows 6 to 10 of the matrix 2 selected by the electronic circuit 33, a line-shaped focus of the sound lobe is obtained if the electrodes of the upper flat side of the matrix 2 are at zero potential. If the electrodes of the lower flat side of the matrix 2 are connected to zero potential and the electrodes of the upper flat side are driven by the electronic circuit 96, a point-shaped focus of the sound lobe is obtained. With this embodiment of the transducer array, radiation can be sent through the body to be tested at different angles and a fault that is found can be examined in greater detail by the special arrangement of the ultrasonic oscillator groups in conjunction with a particular drive by suitable adjustment of the nearly point-shaped or nearly line-shaped focusing.

I claim:

1. An ultrasonic transducer array comprising:
   a. a matrix of ultrasonic oscillators, each comprising a matrix of jointly controlled column-like transducer elements, the end faces of which are arranged in the plane of one of the flat sides of the matrix, the transducers of each oscillator connected to a common control electrode;
   b. on one flat side of the matrix, a separate common control line for each row of ultrasonic oscillators; and
   c. on the opposite flat side of the matrix, a separate common control line connected to electrodes of groups of ultrasonic oscillators arranged concentrically to each other.

2. An ultrasonic transducer array according to claim 1, wherein the length of said column-like transducer elements is, at least approximately, equal to one-half of the wavelength of the ultrasound and the width of which is at most one-half of its length.

3. An ultrasonic transducer array according to claim 1, and further including means for connecting all control electrodes of the ultrasonic oscillators on each respective flat side of the matrix to a common potential.

4. An ultrasonic transducer array according to claim 3, and further including a transmitter and receiver arrangement including an ultrasonic transmitter and ultrasonic receiver for each control electrode with an electronic double-throw switching system associated with the electrodes of each of the two flat sides of the matrix for switching between said ultrasonic transmitters and ultrasonic receivers.

5. An ultrasonic transducer array according claim 4, wherein said means for connecting comprise a first double throw switch for connecting the control lines for the electrodes on the one flat side of the matrix to a common potential and a second double throw switch for connecting the control lines for the electrodes on the opposite flat side of the matrix to a common potential.

6. An ultrasonic transducer array according to claim 5 and further including a series circuit of delay stages of a linear electronic delay chain and of a square law electronic delay chain for the electrodes of the rows of the ultrasonic oscillators on the one flat side of the matrix and means for switching said delay stages so as to be between said transmitters and receivers and said electrodes.

7. An ultrasonic transducer array according to claim 6, and further comprising a further electronic delay stage of a square-law delay chain and means for connecting the concentric electrode groups of the ultrasonic oscillators on the opposite flat side of the matrix electronically to its associated ultrasonic transmitter as well as to its associated ultrasonic receiver through said further electronic delay stage.

8. An ultrasonic transducer array according to claim 1, wherein each of the concentric electrode groups of the ultrasonic oscillators on a flat side of the matrix forms a ring.

9. An ultrasonic transducer array according to claim 1, wherein each of the concentric electrode groups of the ultrasonic oscillators forms a star.

* * * * *